United States Patent

Psaar et al.

Patent Number: 4,897,494
Date of Patent: Jan. 30, 1990

[54] BIS(INDOLYL)ETHYLENE PROCESS

[75] Inventors: Hubertus Psaar; Horst Berneth, both of Leverkusen, Fed. Rep. of Germany

[73] Assignee: Bayer Aktiengesellschaft, Leverkusen, Fed. Rep. of Germany

[21] Appl. No.: 261,945

[22] Filed: Oct. 24, 1988

[30] Foreign Application Priority Data

Nov. 11, 1987 [DE]   Fed. Rep. of Germany ....... 3738237

[51] Int. Cl.$^4$ ............................................ C07D 403/06
[52] U.S. Cl. .................................................... 548/455
[58] Field of Search ......................................... 548/455

[56] References Cited

U.S. PATENT DOCUMENTS 2,154,926  4/1939  Wolff et al. ......................... 548/455
4,510,156  4/1985  Kabbe et al. ..................... 548/455 X

FOREIGN PATENT DOCUMENTS 512477  9/1939  United Kingdom ............... 548/455

Primary Examiner—David B. Springer
Attorney, Agent, or Firm—Sprung Horn Kramer & Woods

[57] ABSTRACT

Bis(indolyl)ethylenes of the formula

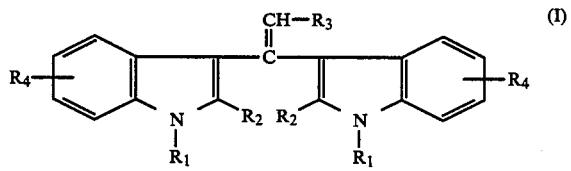

wherein
$R_1$ denotes hydrogen, alkyl, aralkyl or aryl,
$R_2$ denotes hydrogen, alkyl or aryl,
$R_3$ denotes hydrogen, alkyl, alkenyl, COOH or aryl and
$R_4$ denotes hydrogen, alkyl, alkoxy, cycloalkoxy or halogen, and these substituents, in turn, can carry non-ionic radicals or a carboxyl group, are obtained by reaction of indoles of the formula

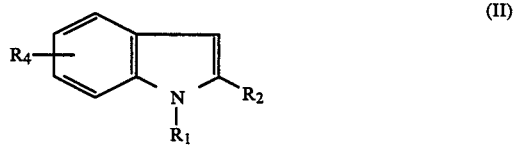

with carboxylic acids of the formula

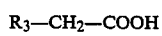

their chlorides, esters, for example alkyl esters, or anhydrides in the presence of phosphorus oxychloride.

7 Claims, No Drawings

BIS(INDOLYL)ETHYLENE PROCESS

The invention relates to a process for the preparation of bis(indolyl)ethylenes of the formula

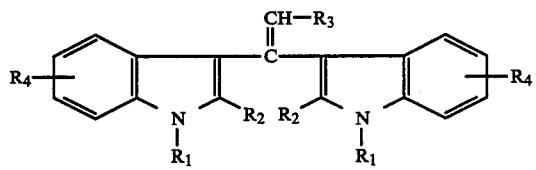

wherein
- $R_1$ denotes hydrogen, alkyl, aralkyl or aryl,
- $R_2$ denotes hydrogen, alkyl or aryl,
- $R_3$ denotes hydrogen, alkyl, alkenyl, COOH or aryl and
- $R_4$ denotes hydrogen, alkyl, alkoxy, cycloalkoxy or halogen, and these substituents, in turn, can carry non-ionic radicals or a carboxyl group,
by reaction of indoles of the formula

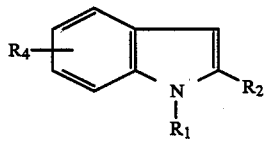

with carboxylic acids of the formula $$R_3\text{—}CH_2\text{—}COOH \qquad (III)$$

their chlorides, esters, for example alkyl esters, or anhydrides in the presence of phosphorus oxychloride.

Preferably, alkoxy stands for $C_1$-$C_{12}$-alkoxy, alkyl stands for $C_1$-$C_{12}$-alkyl, alkenyl stands for $C_2$-$C_{12}$-alkenyl, aryl stands for phenyl, aralkyl stands for benzyl or phenethyl, cycloalkoxy stands for cyclohexoxy or cyclopentoxy and halogen stands for fluorine, chlorine or bromine, in particular chlorine.

Non-ionic radicals which should be mentioned are, for example, halogen, in particular chlorine, $C_1$-$C_4$-alkoxy, cyano and for the cyclic substituents, in addition $C_1$-$C_4$-alkyl.

The preferred reaction temperature is 50° C. to 105° C., and the preferred reaction time is between 20 minutes and 3 hours. The molar ratio of (II):(III) should preferably be 2:1 at most.

Phosphorus oxychloride is advantageously employed in a molar ratio of 1.5 to 2:1 relative to (III) or its derivatives.

The reaction can be carried out with or without solvent, it being intended that the amount of phosphorus oxychloride is measured in the last case such that this simultaneously acts as the solvent. Aromatics, alkylated aromatics or chlorinated aromatics can be employed as the solvent. Suitable solvents are, for example, toluene, xylene, chlorobenzene or dichlorobenzene.

The process makes possible the preparation of the compounds (I) in a simple manner with high yield.

The invention further relates to bis(indolyl)ethylenes of the formula

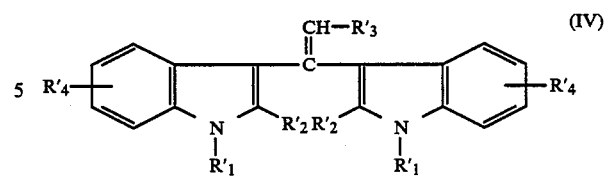

wherein
either
(a) $R'_1$ denotes $C_2$-$C_{12}$-alkyl or benzyl,
  $R'_2$ and $R'_3$ denote hydrogen, alkyl or benzyl,
  $R'_4$ denotes hydrogen, alkyl, alkoxy or halogen, and phenyl and benzyl, each of which can be substituted by alkyl, alkoxy or halogen, or
(b) $R'_1$ denotes hydrogen, alkyl or benzyl which can be substituted by alkyl, alkoxy or halogen, and
  $R'_4$ denotes alkyl, alkoxy or halogen, and
  $R'_2$ and $R'_3$ have the abovementioned meaning, or
(c) $R'_1$ denotes hydrogen, alkyl, or benzyl which can be substituted by alkyl, alkoxy or halogen,
  $R'_2$ denotes phenyl which can be substituted by alkyl, alkoxy or halogen,
  $R'_3$ denotes hydrogen, alkyl, or phenyl which can be substituted by alkyl, alkoxy or halogen, and
  $R'_4$ denotes hydrogen, alkyl, alkoxy or halogen, or
(d) $R'_1$ denotes hydrogen, alkyl, or benzyl which can be substituted by alkyl, alkoxy or halogen,
  $R'_2$ denotes phenyl,
  $R'_3$ denotes alkyl or phenyl and
  $R'_4$ denotes hydrogen, alkyl, alkoxy or halogen, and wherein alkyl—when not named separately—stands for $C_1$-$C_{12}$-alkyl and alkoxy stands for $C_1$-$C_{12}$-alkoxy and the alkyl radicals can be substituted by chlorine, cyano or carboxyl.

The compounds (c) and (d) are particularly preferred.

The compounds of the formula (I) are valuable intermediates for colour formers, which are described, for example, in DE-A-3,738,240.

EXAMPLE 1

20.7 parts by weight of 1-methyl-2-phenylindole are heated to 80° to 90° C. with stirring in 30 ml of phosphorus oxychloride. At this temperature, 5.3 parts by weight of acetic anhydrides are added dropwise and the batch is stirred for 30 minutes at 100° C. The mixture is then discharged onto 200 parts by weight of ice water, rendered alkaline with 10% strength sodium hydroxide solution, stirred for 15 hours at room temperature, and the precipitate is filtered off with suction and recrystallized from dimethylformamide.

Yield: 20.3 parts by weight; m.p.: 192°–194° C.

The compound has the formula:

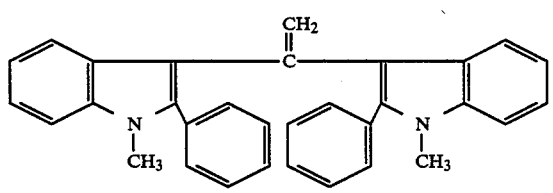

EXAMPLE 2

20.7 parts by weight of 1-methyl-2-phenylindole are heated to 90° C. in 50 ml phosphorus oxychloride and 4.9 parts by weight of propionic acid are added dropwise at this temperature. After 30 minutes, the mixture is cooled to room temperature and 100 ml of methanol are slowly added. The batch is subsequently stirred into a mixture of 500 ml of conc. ammonia and 500 ml of water. The product is filtered off with suction, stirred with methanol and dried at 50° C. in vacuo.

Yield: 22.1 parts by weight.
m.p.: 184°–186° C.
The compound has the formula:

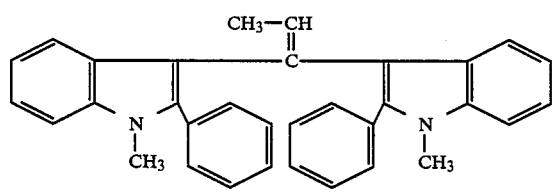

EXAMPLE 3

If 10 parts by weight of butyrolactone are added dropwise to the batch instead of propionic acid according to Example 2, then the bis(indolyl)ethylene of the formula

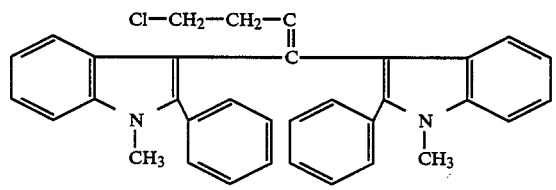

is obtained.
Yield: 24.5 parts by weight.
m.p.: 101°–103° C.
The compounds of the formula

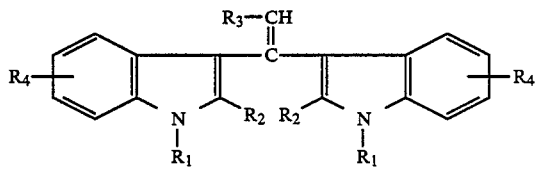

are prepared analogously to Example 1.

| Example | $R_1$ | $R_2$ | $R_3$ | $R_4$ | m.p. |
|---|---|---|---|---|---|
| 4 | $CH_3$ | $CH_3$ | H | H | 173° C. |
| 5 | $CH_3$ | H | H | H | 142–143° C. |
| 6 | $CH_3$ | $CH_3$ | $CH_3$ | H | 101–103° C. |
| 7 | $C_4H_9$ | $CH_3$ | H | H | |
| 8 | $CH_3$ | $CH_3$ | $C_{10}H_{21}$ | H | 97–99° C. |
| 9 | $CH_3$ | $C_6H_5$ | $CH_2$—COOH | H | 108–112° C. |
| 10 | $CH_3$ | $C_6H_5$ | $CH=CH_2$ | H | 165–167° C. |
| 11 | $C_2H_4CN$ | $C_6H_5$ | H | H | 210° C. |
| 12 | $C_2H_4COOH$ | $C_6H_5$ | H | H | 220° C. |
| 13 | $C_4H_9$ | $C_6H_5$ | H | H | 89–91° C. |
| 14 | $C_6H_5CH_2$ | $C_6H_5$ | H | H | 238–240° C. |
| 15 | $C_6H_5CH_2$ | $CH_3$ | H | H | 148–149° C. |
| 16 | $CH_3$ | $C_6H_4, 4\text{-}OCH_3$ | H | H | 172–174° C. |
| 17 | $CH_3$ | $C_6H_4, 4\text{-}Cl$ | H | H | 210° C. |
| 18 | $CH_3$ | $C_6H_5$ | H | 6-Cl | 214–217° C. |
| 19 | $CH_3$ | $C_6H_5$ | H | 5-$CH_3$ | 225–227° C. |
| 20 | $C_2H_5$ | $C_6H_5$ | H | H | 160° C. |
| 21 | $CH_3$ | $C_6H_5$ | Cl | H | 182,5° C. |
| 22 | H | $C_6H_5$ | H | H | 244–246° C. |
| 23 | H | $C_6H_5$ | $CH_3$ | H | 169° C. |
| 24 | $C_6H_5CH_2$ | $C_6H_5$ | $CH_3$ | H | 80° C. |

We claim:
1. A process for the preparation of a bis(indolyl)ethylene of the formula

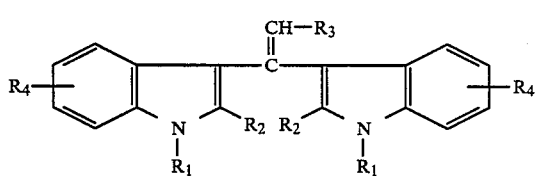

wherein
$R_1$ denotes hydrogen, $C_1$-$C_{12}$-alkyl, aralkyl, wherein said aralkyl is benzyl or phenylethyl, or phenyl,
$R_2$ denotes hydrogen, $C_1$-$C_{12}$-alkyl, or phenyl,
$R_3$ denotes hydrogen, $C_1$-$C_{12}$-alkyl, $C_2$-$C_{12}$-alkenyl, COOH or phenyl and
$R_4$ denotes hydrogen, $C_1$-$C_{12}$-alkyl, $C_1$-$C_{12}$-alkoxy, cycloalkoxy or halogen $C_1$-$C_4$ alkoxy, said alkyl being unsubstituted or substituted by a halogen, $C_1$-$C_4$-alkoxy cyano or a carboxyl group, said aralkyl being unsubstituted or substituted by halogen, cyano, $C_1$-$C_4$-alkoxy or a carboxyl group, said phenyl being unsubstituted or substituted by a halogen, $C_1$-$C_4$-alkoxy, cyano, $C_1$-$C_4$-alkyl or a carboxyl group, said alkoxy being unsubstituted or substituted by a halogen, cyano or a carboxyl group, said cycloalkoxy being unsubstituted or substituted by a halogen, cyano or a carboxyl group,
by reaction of an indole of the formula

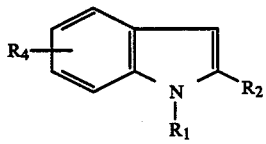

with a carboxylic acid of the formula

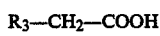

, their chlorides, esters, or anhydrides in the presence of phosphorus oxychloride.

2. A process according to claim 1, wherein the reaction is carried out at 50° C. to 105° C. during the course of 20 minutes to 3 hours.

3. A process according to claim 1, wherein the reaction is carried out using a molar ratio of phosphorus oxychloride to carboxylic acid or its derivatives of 1.5 to 2:1.

4. A process according to claim 1, wherein said halogen is fluorine, chlorine or bromine.

5. A process according to claim 1, wherein said halogen is chlorine.

6. A process according to claim 1, wherein said phenyl is substituted by chlorine or —OCH$_3$.

7. A process according to claim 1, wherein said cycloalkoxy is cyclohexoxy or cyclopentoxy.

* * * * *

UNITED STATES PATENT AND TRADEMARK OFFICE
CERTIFICATE OF CORRECTION

PATENT NO. : 4,897,494

DATED : January 30, 1990

INVENTOR(S) : Psaar et al.

It is certified that error appears in the above-identified patent and that said Letters Patent is hereby corrected as shown below:

Col. 4, claim 1 line 58    After " $C_1-C_4$-alkoxy " insert -- , --

Signed and Sealed this

Nineteenth Day of November, 1991

Attest:

HARRY F. MANBECK, JR.

*Attesting Officer*    *Commissioner of Patents and Trademarks*